(12) United States Patent
Dawson

(10) Patent No.: US 11,944,817 B2
(45) Date of Patent: Apr. 2, 2024

(54) VARIABLE AMPLITUDE SIGNALS FOR NEUROLOGICAL THERAPY, AND ASSOCIATED SYSTEMS AND METHODS

(71) Applicant: Nevro Corp., Redwood City, CA (US)

(72) Inventor: Chris Dawson, Westfield, IN (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 17/900,681

(22) Filed: Aug. 31, 2022

(65) Prior Publication Data

US 2023/0248974 A1 Aug. 10, 2023

Related U.S. Application Data

(63) Continuation of application No. 16/420,037, filed on May 22, 2019, now Pat. No. 11,458,317, which is a
(Continued)

(51) Int. Cl.
*A61N 1/36* (2006.01)
*A61N 1/05* (2006.01)

(52) U.S. Cl.
CPC ....... *A61N 1/36071* (2013.01); *A61N 1/0551* (2013.01); *A61N 1/36017* (2013.01); *A61N 1/36021* (2013.01); *A61N 1/36171* (2013.01)

(58) Field of Classification Search
None
See application file for complete search history.

(56) References Cited

U.S. PATENT DOCUMENTS

| 3,774,618 A | 11/1973 | Avery |
| 4,014,347 A | 3/1977 | Halleck et al. |

(Continued)

FOREIGN PATENT DOCUMENTS

| EP | 1331965 A2 | 8/2003 |
| EP | 2243510 | 10/2010 |

(Continued)

OTHER PUBLICATIONS

Hayt et al., "Engine Circuit Analysis," McGraw-Hill Book Company, Fourth Edition, 1986, 18 pages.
(Continued)

*Primary Examiner* — Ankit D Tejani
(74) *Attorney, Agent, or Firm* — Perkins Coie LLP

(57) ABSTRACT

Variable amplitude signals for neurological therapy, and associated systems and methods are disclosed. A representative method includes activating automatic delivery of an electrical therapy signal to a patient's spinal cord region at a frequency in a frequency range between 1.5 kHz and 100 kHz, via at least one signal delivery contact carried by an implanted signal delivery device. The delivery can include repeatedly and automatically delivering the electrical therapy signal at each of multiple therapy signal amplitudes to the at least one signal delivery contact, without the therapy signal generating paresthesia in the patient. The foregoing process can be used as a screening tool to screen responders from non-responders in the context of a non-paresthesia-generating therapy, and/or can be used during long-term treatment, for example, for chronic pain.

25 Claims, 8 Drawing Sheets

Related U.S. Application Data continuation of application No. 15/376,221, filed on Dec. 12, 2016, now Pat. No. 10,300,277.

(60) Provisional application No. 62/267,141, filed on Dec. 14, 2015.

(56) References Cited

U.S. PATENT DOCUMENTS

| | | |
|---|---|---|
| 4,019,519 A | 4/1977 | Geerling |
| 4,210,151 A | 7/1980 | Keller, Jr. |
| 4,257,429 A | 3/1981 | Dickhudt et al. |
| 4,340,063 A | 7/1982 | Maurer |
| 4,467,800 A | 8/1984 | Zytkovicz |
| 4,899,750 A | 2/1990 | Ekwall |
| 5,016,635 A | 5/1991 | Graupe |
| 5,031,618 A | 7/1991 | Mullett |
| 5,042,486 A | 8/1991 | Pfeiler et al. |
| 5,052,375 A | 10/1991 | Stark et al. |
| 5,063,929 A | 11/1991 | Bartelt et al. |
| 5,069,211 A | 12/1991 | Bartelt et al. |
| 5,078,140 A | 1/1992 | Kwoh |
| 5,143,081 A | 9/1992 | Young et al. |
| 5,159,926 A | 11/1992 | Ljungstroem |
| 5,184,617 A | 2/1993 | Harris et al. |
| 5,211,165 A | 5/1993 | Dumoulin et al. |
| 5,222,494 A | 6/1993 | Baker, Jr. |
| 5,223,226 A | 6/1993 | Wittmer et al. |
| 5,224,475 A | 7/1993 | Berg et al. |
| 5,257,636 A | 11/1993 | White |
| 5,325,873 A | 7/1994 | Hirschi et al. |
| 5,335,657 A | 8/1994 | Terry, Jr. et al. |
| 5,342,409 A | 8/1994 | Mullett |
| 5,354,320 A | 10/1994 | Schaldach et al. |
| 5,375,596 A | 12/1994 | Twiss et al. |
| 5,423,329 A | 6/1995 | Ergas |
| 5,425,367 A | 6/1995 | Shapiro et al. |
| 5,540,730 A | 7/1996 | Terry, Jr. et al. |
| 5,641,326 A | 6/1997 | Adams |
| 5,643,330 A | 7/1997 | Holsheimer et al. |
| 5,702,429 A | 12/1997 | King |
| 5,727,553 A | 3/1998 | Saad |
| 5,782,884 A | 7/1998 | Stotts et al. |
| 5,814,092 A | 9/1998 | King |
| 5,843,146 A | 12/1998 | Cross, Jr. |
| 5,871,487 A | 2/1999 | Warner et al. |
| 5,891,179 A | 4/1999 | Er et al. |
| 5,893,883 A | 4/1999 | Torgerson |
| 5,913,882 A | 6/1999 | King |
| 5,938,690 A | 8/1999 | Law |
| 5,983,141 A | 11/1999 | Sluijter et al. |
| 6,052,624 A | 4/2000 | Mann |
| 6,155,267 A | 12/2000 | Nelson |
| 6,159,163 A | 12/2000 | Strauss et al. |
| 6,192,278 B1 | 2/2001 | Werner et al. |
| 6,198,963 B1 | 3/2001 | Haim et al. |
| 6,208,894 B1 | 3/2001 | Schulman et al. |
| 6,236,892 B1 | 5/2001 | Feler |
| 6,308,102 B1 | 10/2001 | Sieracki et al. |
| 6,319,241 B1 | 11/2001 | King et al. |
| 6,341,236 B1 | 1/2002 | Osorio et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,393,328 B1 | 5/2002 | McGraw et al. |
| 6,438,418 B1 | 8/2002 | Swerdlow et al. |
| 6,440,090 B1 | 8/2002 | Schallhorn |
| 6,461,357 B1 | 10/2002 | Sharkey et al. |
| 6,474,341 B1 | 11/2002 | Hunter et al. |
| 6,516,227 B1 | 2/2003 | Meadows et al. |
| 6,574,507 B1 | 6/2003 | Bonnet |
| 6,587,727 B2 | 7/2003 | Osorio et al. |
| 6,609,030 B1 | 8/2003 | Rezai et al. |
| 6,609,032 B1 | 8/2003 | Woods et al. |
| 6,622,048 B1 | 9/2003 | Mann |
| 6,659,968 B1 | 12/2003 | McClure |
| 6,671,556 B2 | 12/2003 | Osorio et al. |
| 6,712,772 B2 | 3/2004 | Cohen et al. |
| 6,740,072 B2 | 5/2004 | Starkweather et al. |
| 6,757,561 B2 | 6/2004 | Rubin et al. |
| 6,862,480 B2 | 3/2005 | Cohen et al. |
| 6,871,090 B1 | 3/2005 | He et al. |
| 6,873,872 B2 | 3/2005 | Gluckman et al. |
| 6,875,571 B2 | 4/2005 | Crabtree et al. |
| 6,895,280 B2 | 5/2005 | Meadows et al. |
| 6,909,917 B2 | 6/2005 | Woods et al. |
| 6,920,357 B2 | 7/2005 | Osorio et al. |
| 6,947,792 B2 | 9/2005 | Ben-Haim et al. |
| 6,950,707 B2 | 9/2005 | Whitehurst |
| 6,961,618 B2 | 11/2005 | Osorio et al. |
| 6,978,171 B2 | 12/2005 | Goetz et al. |
| 6,993,384 B2 | 1/2006 | Bradley et al. |
| 7,010,345 B2 | 3/2006 | Hill et al. |
| 7,020,523 B1 | 3/2006 | Lu et al. |
| 7,024,246 B2 | 4/2006 | Acosta et al. |
| 7,024,247 B2 | 4/2006 | Gliner et al. |
| 7,050,856 B2 | 5/2006 | Stypulkowski |
| 7,082,333 B1 | 7/2006 | Bauhahn et al. |
| 7,110,821 B1 | 9/2006 | Ross |
| 7,123,967 B2 | 10/2006 | Weinberg |
| 7,127,296 B2 | 10/2006 | Bradley |
| 7,142,923 B2 | 11/2006 | North et al. |
| 7,174,215 B2 | 2/2007 | Bradley |
| 7,177,690 B2 | 2/2007 | Woods |
| 7,180,760 B2 | 2/2007 | Varrichio et al. |
| 7,184,837 B2 | 2/2007 | Goetz |
| 7,191,012 B2 | 3/2007 | Boveja et al. |
| 7,206,632 B2 | 4/2007 | King |
| 7,206,642 B2 | 4/2007 | Pardo et al. |
| 7,212,867 B2 | 5/2007 | Van Venrooij et al. |
| 7,236,834 B2 | 6/2007 | Christopherson et al. |
| 7,239,920 B1 | 7/2007 | Thacker et al. |
| 7,239,926 B2 | 7/2007 | Goetz |
| 7,241,283 B2 | 7/2007 | Putz |
| 7,242,984 B2 | 7/2007 | DiLorenzo |
| 7,244,150 B1 | 7/2007 | Brase et al. |
| 7,252,090 B2 | 8/2007 | Goetz |
| 7,263,402 B2 | 8/2007 | Thacker et al. |
| 7,266,412 B2 | 9/2007 | Stypulkowski |
| 7,286,878 B2 | 10/2007 | Stypulkowski |
| 7,289,851 B2 | 10/2007 | Gunderson et al. |
| 7,289,852 B2 | 10/2007 | Helfinstine et al. |
| 7,295,876 B1 | 11/2007 | Erickson |
| 7,313,440 B2 | 12/2007 | Miesel |
| 7,317,948 B1 | 1/2008 | King et al. |
| 7,329,262 B2 | 2/2008 | Gill |
| 7,343,200 B2 | 3/2008 | Litvak et al. |
| 7,349,739 B2 | 3/2008 | Harry et al. |
| 7,381,441 B2 | 6/2008 | Leung et al. |
| 7,386,348 B2 | 6/2008 | North et al. |
| 7,403,821 B2 | 7/2008 | Haugland et al. |
| 7,406,351 B2 | 7/2008 | Wesselink |
| 7,414,534 B1 | 8/2008 | Kroll et al. |
| 7,425,142 B1 | 9/2008 | Putz |
| 7,444,181 B2 | 10/2008 | Shi et al. |
| 7,447,545 B2 | 11/2008 | Heruth et al. |
| 7,450,992 B1 | 11/2008 | Cameron |
| 7,463,927 B1 | 12/2008 | Chaouat |
| 7,483,747 B2 | 1/2009 | Gliner et al. |
| 7,489,970 B2 | 2/2009 | Lee et al. |
| 7,555,346 B1 | 6/2009 | Woods et al. |
| 7,571,001 B2 | 8/2009 | Thacker et al. |
| 7,603,175 B2 | 10/2009 | Voelkel |
| 7,606,622 B2 | 10/2009 | Reeve |
| 7,617,002 B2 | 11/2009 | Goetz |
| 7,634,315 B2 | 12/2009 | Cholette |
| 7,647,101 B2 | 1/2010 | Libbus et al. |
| 7,657,317 B2 | 2/2010 | Thacker et al. |
| 7,660,628 B2 | 2/2010 | Libbus et al. |
| 7,702,379 B2 | 4/2010 | Avinash et al. |
| 7,706,889 B2 | 4/2010 | Gerber et al. |
| 7,747,330 B2 | 6/2010 | Nolan et al. |
| 7,751,900 B2 | 7/2010 | Voelkel |
| 7,783,349 B2 | 8/2010 | Libbus et al. |
| 7,799,021 B2 | 9/2010 | Leung et al. |

(56) References Cited

U.S. PATENT DOCUMENTS

| | | |
|---|---|---|
| 7,801,601 B2 | 9/2010 | Maschino et al. |
| 7,801,619 B2 | 9/2010 | Gerber et al. |
| 7,801,621 B1 | 9/2010 | Thacker et al. |
| 7,819,909 B2 | 10/2010 | Goetz et al. |
| 7,826,901 B2 | 11/2010 | Lee et al. |
| 7,831,305 B2 | 11/2010 | Gliner |
| 7,831,307 B1 | 11/2010 | Moffitt |
| 7,853,322 B2 | 12/2010 | Bourget et al. |
| 7,853,323 B2 | 12/2010 | Goetz |
| 7,856,277 B1 | 12/2010 | Thacker et al. |
| 7,872,884 B2 | 1/2011 | Parramon et al. |
| 7,873,418 B2 | 1/2011 | Stypulkowski |
| 7,881,805 B2 | 2/2011 | Bradley et al. |
| 7,945,330 B2 | 5/2011 | Gliner et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,966,073 B2 | 6/2011 | Pless et al. |
| 7,996,055 B2 | 8/2011 | Hauck et al. |
| 8,016,776 B2 | 9/2011 | Bourget et al. |
| 8,095,220 B2 | 1/2012 | Lee et al. |
| 8,116,878 B1 | 2/2012 | Palmer |
| 8,121,703 B1 | 2/2012 | Palmer |
| 8,128,600 B2 | 3/2012 | Gill |
| 8,131,357 B2 | 3/2012 | Bradley et al. |
| 8,170,675 B2 | 5/2012 | Alataris et al. |
| 8,180,445 B1 | 5/2012 | Moffitt |
| 8,197,494 B2 | 6/2012 | Jaggi et al. |
| 8,209,021 B2 | 6/2012 | Alataris et al. |
| 8,209,028 B2 | 6/2012 | Skelton et al. |
| 8,260,432 B2 | 9/2012 | DiGiore et al. |
| 8,355,791 B2 | 1/2013 | Moffitt |
| 8,355,797 B2 | 1/2013 | Caparso et al. |
| 8,423,147 B2 | 4/2013 | Alataris et al. |
| 8,428,748 B2 | 4/2013 | Alataris et al. |
| 8,457,759 B2 | 6/2013 | Parker et al. |
| 8,498,710 B2 | 7/2013 | Walker et al. |
| 8,626,312 B2 | 1/2014 | King et al. |
| 8,712,533 B2 | 4/2014 | Alataris et al. |
| 8,712,534 B2 | 4/2014 | Wei |
| 8,712,535 B2 | 4/2014 | Walker et al. |
| 9,061,154 B2 | 6/2015 | Parker et al. |
| 9,248,293 B2 | 2/2016 | Walker et al. |
| 9,278,222 B2 | 3/2016 | Thacker et al. |
| 9,295,840 B1 | 3/2016 | Thacker et al. |
| 9,399,137 B2 | 7/2016 | Parker et al. |
| 9,517,344 B1 | 12/2016 | Bradley |
| 9,669,219 B2 | 6/2017 | Caparso |
| 9,700,724 B2 | 7/2017 | Liu et al. |
| 9,731,133 B1 | 8/2017 | Thacker et al. |
| 9,814,884 B2 | 11/2017 | Parker et al. |
| 9,827,423 B2 | 11/2017 | Walker |
| 9,895,538 B1 | 2/2018 | Thacker |
| 9,937,348 B1 | 4/2018 | Bradley |
| 10,086,204 B2* | 10/2018 | Grill, Jr. ............ A61N 1/36067 |
| 10,149,978 B1* | 12/2018 | Park .................... A61N 1/36175 |
| 10,207,109 B2 | 2/2019 | Zhu et al. |
| 10,300,277 B1 | 5/2019 | Dawson |
| 10,420,935 B2 | 9/2019 | Illegems |
| 10,493,275 B2 | 12/2019 | Alataris et al. |
| 10,537,740 B2 | 1/2020 | Cabunaru |
| 11,235,153 B2 | 2/2022 | Kibler et al. |
| 11,458,317 B1 | 10/2022 | Dawson |
| 2002/0068930 A1 | 6/2002 | Tasto et al. |
| 2002/0165586 A1 | 11/2002 | Hill et al. |
| 2003/0004549 A1 | 1/2003 | Hill et al. |
| 2003/0093134 A1 | 5/2003 | Bradley |
| 2003/0100931 A1 | 5/2003 | Mullett |
| 2003/0135241 A1 | 7/2003 | Leonard et al. |
| 2003/0135248 A1 | 7/2003 | Stypulkowski |
| 2003/0153959 A1 | 8/2003 | Thacker et al. |
| 2003/0195582 A1 | 10/2003 | Mann |
| 2003/0199952 A1 | 10/2003 | Stolz et al. |
| 2003/0204221 A1 | 10/2003 | Rodriguez et al. |
| 2003/0208244 A1 | 11/2003 | Stein et al. |
| 2003/0212445 A1 | 11/2003 | Weinberg |
| 2004/0015202 A1 | 1/2004 | Chandler et al. |
| 2004/0034394 A1 | 2/2004 | Woods et al. |
| 2004/0093093 A1 | 5/2004 | Andrews |
| 2004/0116978 A1 | 6/2004 | Bradley |
| 2004/0138516 A1 | 7/2004 | Osorio et al. |
| 2004/0167584 A1 | 8/2004 | Carroll et al. |
| 2004/0176812 A1 | 9/2004 | Knudson et al. |
| 2004/0186544 A1 | 9/2004 | King |
| 2004/0199214 A1 | 10/2004 | Merfeld et al. |
| 2004/0210290 A1 | 10/2004 | Omar-Pasha |
| 2004/0215286 A1 | 10/2004 | Stypulkowski |
| 2005/0004417 A1 | 1/2005 | Nelson et al. |
| 2005/0004638 A1 | 1/2005 | Cross |
| 2005/0033381 A1 | 2/2005 | Carter et al. |
| 2005/0038489 A1 | 2/2005 | Grill |
| 2005/0049664 A1 | 3/2005 | Harris et al. |
| 2005/0060001 A1 | 3/2005 | Singhal et al. |
| 2005/0060007 A1 | 3/2005 | Goetz |
| 2005/0209645 A1 | 9/2005 | Heruth et al. |
| 2005/0209655 A1 | 9/2005 | Bradley et al. |
| 2005/0245987 A1 | 11/2005 | Woods et al. |
| 2006/0089697 A1 | 4/2006 | Cross et al. |
| 2006/0111754 A1 | 5/2006 | Rezai et al. |
| 2006/0116742 A1 | 6/2006 | De Ridder |
| 2006/0122654 A1 | 6/2006 | Bradley et al. |
| 2006/0135998 A1 | 6/2006 | Libbus et al. |
| 2006/0161236 A1 | 7/2006 | King |
| 2006/0190048 A1 | 8/2006 | Gerber |
| 2006/0195159 A1 | 8/2006 | Bradley et al. |
| 2006/0235472 A1 | 10/2006 | Goetz et al. |
| 2006/0247732 A1 | 11/2006 | Wesselink |
| 2006/0253174 A1 | 11/2006 | King |
| 2006/0253182 A1 | 11/2006 | King |
| 2006/0259079 A1 | 11/2006 | King |
| 2006/0259099 A1 | 11/2006 | Goetz et al. |
| 2006/0293720 A1 | 12/2006 | DiLorenzo |
| 2007/0039625 A1 | 2/2007 | Heruth et al. |
| 2007/0066995 A1 | 3/2007 | Strother et al. |
| 2007/0073357 A1 | 3/2007 | Rooney et al. |
| 2007/0100378 A1 | 5/2007 | Maschino |
| 2007/0129774 A1 | 6/2007 | Bourget et al. |
| 2007/0135868 A1 | 6/2007 | Shi et al. |
| 2007/0142874 A1 | 6/2007 | John |
| 2007/0150029 A1 | 6/2007 | Bourget et al. |
| 2007/0156207 A1 | 7/2007 | Kothandaraman et al. |
| 2007/0162088 A1 | 7/2007 | Chen et al. |
| 2007/0179559 A1 | 8/2007 | Giftakis et al. |
| 2007/0179579 A1 | 8/2007 | Feler et al. |
| 2007/0208394 A1 | 9/2007 | King et al. |
| 2007/0213773 A1 | 9/2007 | Hill et al. |
| 2007/0213789 A1 | 9/2007 | Nolan et al. |
| 2007/0245318 A1 | 10/2007 | Goetz et al. |
| 2007/0249968 A1 | 10/2007 | Miesel et al. |
| 2007/0253928 A1 | 11/2007 | Roy et al. |
| 2007/0255118 A1 | 11/2007 | Miesel et al. |
| 2007/0265679 A1 | 11/2007 | Bradley et al. |
| 2007/0265681 A1 | 11/2007 | Gerber et al. |
| 2007/0270921 A1 | 11/2007 | Strother et al. |
| 2007/0276450 A1 | 11/2007 | Meadows et al. |
| 2007/0276453 A1 | 11/2007 | Hill et al. |
| 2008/0015657 A1 | 1/2008 | Haefner |
| 2008/0046036 A1 | 2/2008 | King et al. |
| 2008/0046052 A1 | 2/2008 | Werder et al. |
| 2008/0051839 A1 | 2/2008 | Libbus et al. |
| 2008/0064980 A1 | 3/2008 | Lee et al. |
| 2008/0071325 A1 | 3/2008 | Bradley |
| 2008/0103570 A1 | 5/2008 | Gerber |
| 2008/0109050 A1 | 5/2008 | John |
| 2008/0140150 A1 | 6/2008 | Zhou et al. |
| 2008/0140153 A1 | 6/2008 | Burdulis |
| 2008/0154340 A1 | 6/2008 | Goetz et al. |
| 2008/0156333 A1 | 7/2008 | Galpern et al. |
| 2008/0183256 A1 | 7/2008 | Keacher |
| 2008/0188909 A1 | 8/2008 | Bradley |
| 2008/0215118 A1 | 9/2008 | Goetz et al. |
| 2008/0215119 A1 | 9/2008 | Woods et al. |
| 2008/0234791 A1 | 9/2008 | Arle et al. |
| 2008/0243196 A1 | 10/2008 | Libbus et al. |

(56) References Cited

U.S. PATENT DOCUMENTS

| | | |
|---|---|---|
| 2008/0269843 A1 | 10/2008 | Gerber et al. |
| 2008/0275529 A1 | 11/2008 | North et al. |
| 2008/0281381 A1 | 11/2008 | Gerber et al. |
| 2008/0319511 A1 | 12/2008 | Pless |
| 2008/0319514 A1 | 12/2008 | Shi et al. |
| 2009/0005833 A1 | 1/2009 | Cameron et al. |
| 2009/0018617 A1 | 1/2009 | Skelton et al. |
| 2009/0030476 A1 | 1/2009 | Hargrove |
| 2009/0048643 A1 | 2/2009 | Erickson |
| 2009/0054946 A1 | 2/2009 | Sommer et al. |
| 2009/0112281 A1 | 4/2009 | Miyazawa et al. |
| 2009/0112282 A1 | 4/2009 | Kast et al. |
| 2009/0125079 A1 | 5/2009 | Armstrong et al. |
| 2009/0149917 A1 | 6/2009 | Whitehurst et al. |
| 2009/0204173 A1 | 8/2009 | Fang et al. |
| 2009/0264956 A1 | 10/2009 | Rise et al. |
| 2009/0264957 A1 | 10/2009 | Giftakis et al. |
| 2009/0264967 A1 | 10/2009 | Giftakis et al. |
| 2009/0281594 A1 | 11/2009 | King et al. |
| 2009/0281595 A1 | 11/2009 | King et al. |
| 2009/0281596 A1 | 11/2009 | King et al. |
| 2009/0281599 A1 | 11/2009 | Thacker et al. |
| 2009/0306740 A1 | 12/2009 | Heruth et al. |
| 2009/0306746 A1 | 12/2009 | Blischak |
| 2009/0326608 A1 | 12/2009 | Huynh et al. |
| 2010/0010432 A1 | 1/2010 | Skelton |
| 2010/0010566 A1 | 1/2010 | Thacker et al. |
| 2010/0049280 A1 | 2/2010 | Goetz |
| 2010/0057162 A1 | 3/2010 | Moffitt et al. |
| 2010/0069993 A1 | 3/2010 | Greenspan |
| 2010/0121408 A1 | 5/2010 | Imran et al. |
| 2010/0121409 A1 | 5/2010 | Kothandaraman et al. |
| 2010/0125314 A1 | 5/2010 | Bradley et al. |
| 2010/0131034 A1 | 5/2010 | Gliner et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0185256 A1 | 7/2010 | Hulvershorn |
| 2010/0211135 A1 | 8/2010 | Caparso et al. |
| 2010/0228325 A1 | 9/2010 | Moffitt et al. |
| 2010/0234912 A1 | 9/2010 | Ternes et al. |
| 2010/0274312 A1 | 10/2010 | Alataris et al. |
| 2010/0274314 A1 | 10/2010 | Alataris et al. |
| 2010/0274317 A1 | 10/2010 | Parker et al. |
| 2010/0274320 A1 | 10/2010 | Torgerson |
| 2010/0274336 A1 | 10/2010 | Nguyen-Stella et al. |
| 2010/0277309 A1 | 11/2010 | Anderson |
| 2010/0305631 A1 | 12/2010 | Bradley et al. |
| 2010/0305660 A1 | 12/2010 | Hegi et al. |
| 2010/0312319 A1 | 12/2010 | Barker |
| 2010/0331920 A1 | 12/2010 | DiGiore et al. |
| 2011/0009927 A1 | 1/2011 | Parker et al. |
| 2011/0022141 A1 | 1/2011 | Chen et al. |
| 2011/0029040 A1 | 2/2011 | Walker et al. |
| 2011/0040348 A1 | 2/2011 | Wacnik et al. |
| 2011/0040351 A1 | 2/2011 | Butson et al. |
| 2011/0046697 A1 | 2/2011 | Gerber et al. |
| 2011/0054565 A1 | 3/2011 | Wacnik et al. |
| 2011/0071589 A1 | 3/2011 | Starkebaum et al. |
| 2011/0071593 A1 | 3/2011 | Parker et al. |
| 2011/0087309 A1 | 4/2011 | Stypulkowski |
| 2011/0093051 A1 | 4/2011 | Davis et al. |
| 2011/0118661 A1 | 5/2011 | Pless et al. |
| 2011/0184488 A1 | 7/2011 | De Ridder |
| 2011/0245708 A1 | 10/2011 | Finkel et al. |
| 2011/0301679 A1 | 12/2011 | Rezai |
| 2012/0083857 A1 | 4/2012 | Bradley et al. |
| 2012/0116476 A1 | 5/2012 | Kothandaraman |
| 2012/0130448 A1 | 5/2012 | Woods et al. |
| 2012/0172946 A1 | 7/2012 | Alataris et al. |
| 2012/0253422 A1 | 10/2012 | Thacker et al. |
| 2012/0265268 A1 | 10/2012 | Blum et al. |
| 2012/0265271 A1 | 10/2012 | Goetz |
| 2013/0023950 A1 | 1/2013 | Gauthier |
| 2013/0035740 A1 | 2/2013 | Sharma et al. |
| 2013/0060302 A1 | 3/2013 | Polefko et al. |
| 2013/0066411 A1 | 3/2013 | Thacker et al. |
| 2013/0116754 A1 | 5/2013 | Sharma et al. |
| 2013/0138179 A1* | 5/2013 | DeRidder ............ A61N 1/0551 607/46 |
| 2013/0261694 A1 | 10/2013 | Caparso et al. |
| 2013/0261697 A1 | 10/2013 | Parker |
| 2013/0282078 A1 | 10/2013 | Wacnik |
| 2013/0289667 A1* | 10/2013 | Wacnik ............ A61N 1/36171 607/2 |
| 2013/0310892 A1 | 11/2013 | Parker et al. |
| 2014/0180361 A1 | 1/2014 | Burdick et al. |
| 2014/0067016 A1 | 3/2014 | Kaula |
| 2014/0081349 A1 | 3/2014 | Lee et al. |
| 2014/0081350 A1 | 3/2014 | Zhu |
| 2014/0330338 A1 | 11/2014 | Walker et al. |
| 2014/0343622 A1 | 11/2014 | Alataris |
| 2014/0343623 A1 | 11/2014 | Alves et al. |
| 2015/0005842 A1 | 1/2015 | Lee |
| 2015/0039047 A1 | 2/2015 | Parker |
| 2015/0039048 A1 | 2/2015 | Woods |
| 2015/0151125 A1 | 6/2015 | Zhu |
| 2015/0165209 A1 | 6/2015 | Grandhe |
| 2015/0217113 A1 | 8/2015 | Walker et al. |
| 2015/0321000 A1 | 11/2015 | Rosenbluth |
| 2016/0158551 A1 | 6/2016 | Kent |
| 2016/0175586 A1 | 6/2016 | Edgerton et al. |
| 2016/0271392 A1 | 9/2016 | Vallejo et al. |
| 2017/0189686 A1 | 7/2017 | Steinke et al. |
| 2018/0104494 A1 | 4/2018 | Caparso |
| 2018/0345022 A1 | 12/2018 | Steinke et al. |
| 2019/0022382 A1 | 1/2019 | Gerasimenko et al. |
| 2019/0232064 A1 | 8/2019 | Parker |

FOREIGN PATENT DOCUMENTS

| | | |
|---|---|---|
| EP | 2586491 | 8/2016 |
| JP | 08503648 | 4/1996 |
| JP | 2002090196 | 3/2002 |
| JP | 20020527159 | 8/2002 |
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-0122874 | 4/2001 |
| WO | WO-0245791 | 6/2002 |
| WO | WO-02096512 A1 | 12/2002 |
| WO | WO-2003011361 A2 | 2/2003 |
| WO | WO-2004098698 | 11/2004 |
| WO | WO-2006119046 A1 | 11/2006 |
| WO | WO-2007149018 A1 | 12/2007 |
| WO | WO-2008142402 A1 | 11/2008 |
| WO | WO-2008157182 A1 | 12/2008 |
| WO | WO-2020236946 | 11/2020 |

OTHER PUBLICATIONS

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

North et al., "Spinal Cord Stimulation for Axial Low Back Pain," Spine, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Walsh, Fergus, "Hope over pain relief implant which uses Wii technology," BBC New Health, http://www.bbc.co.uk/news/10509063, accessed Jul. 14, 2010, 3 pages.

Keuchmann C et al., "853 Could Automatic Position Adaptive Stimulation be Useful in Spinal Cord Stimulation," Abstract, Medtronic, Inc., undated, 1 page.

Hofmann et al., "Modified Pulse Shapes for Effective Neural Stimulation," Frontiers in Neuroengineering, Sep. 28, 2011, 10 pages.

(56) References Cited

OTHER PUBLICATIONS

Cappaert et al., "Efficacy of a New Charge-Balanced Biphasic Electrical Stimulus in the Isolated Sciatic Nerve and the Hippocampal Slice," International Journal of Neural Systems, vol. 23, No. 1, 2013, 16 pages.

* cited by examiner

VARIABLE AMPLITUDE SIGNALS FOR NEUROLOGICAL THERAPY, AND ASSOCIATED SYSTEMS AND METHODS

CROSS-REFERENCE TO RELATED APPLICATION

The present application is a continuation of U.S. patent application Ser. No. 16/420,037, filed on May 22, 2019, which is a continuation of U.S. patent application Ser. No. 15/376,221, now issued as U.S. Pat. No. 10,300,277, filed on Dec. 12, 2016, which claims priority to U.S. Provisional Application No. 62/267,141 filed on Dec. 14, 2015, and a incorporated herein by reference in its entirety.

TECHNICAL FIELD

The present technology is directed generally to variable amplitude signals for neurological therapy, and associated systems and methods. A representative method includes automatically sweeping a high frequency therapy signal through multiple amplitudes to determine whether a patient responds to the therapy.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS for the treatment of pain, the signal generator applies electrical pulses to the spinal cord via the electrodes. In conventional SCS, "low frequency" electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In conventional SCS, the patient must first undergo a test (or "trial") period to determine if they are responsive to the therapy before a permanent system is implanted. Responders are identified by meticulously programming multiple programs into an "external" patient-worn trial stimulator system, and instructing the patient to choose the most beneficial program for pain relief. Each of these multiple programs corresponds to stimulating a combination of two or more electrodes out of a total available set of 16 or more electrodes. Because paresthesia over large areas can result in discomfort for most patients, only a few electrodes are activated at a time in each program, to minimize the uncomfortable side effects for the patient. In addition, typical amplitude changes are small and controlled by a trained practitioner in order to avoid shocking the patient.

In contrast to conventional SCS, a form of "high frequency" SCS has been developed that uses high frequency electrical pulses delivered to the spinal cord to treat the patient's sensation of pain without generating paresthesia or otherwise using paresthesia to mask the patient's sensation of pain. Thus, conventional deployment methods, which rely on paresthesia for feedback, may not be adequate for deploying high frequency SCS systems. Accordingly, there is a need for methods of deploying high frequency SCS systems that account for the paresthesia-free aspects of high frequency therapy.

DETAILED DESCRIPTION 1.0 Overview

Figure 1A:
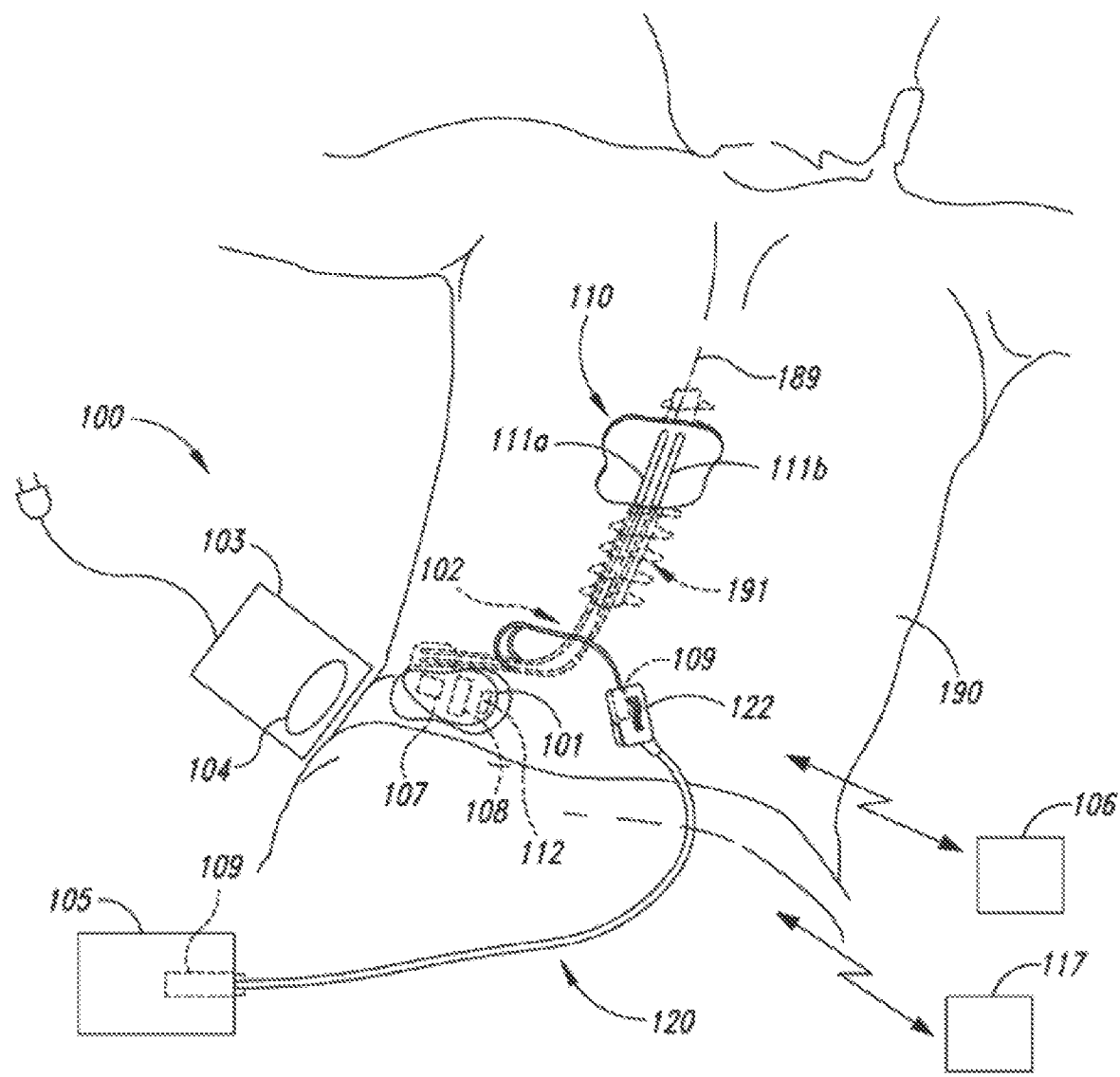
FIG. 1A is a partially schematic illustration of an implantable spinal cord stimulation system positioned at a patient's spine to deliver therapeutic signals in accordance with several embodiments of the present disclosure.

The present technology is directed generally to systems and methods for deploying patient therapy systems, including spinal cord stimulation (SCS) systems, and/or treating patients. For example, in a representative embodiment, the present technology is employed in SCS systems that provide pain relief without generating paresthesia, to identify, early on, those patients who respond favorably to the therapy. The technology can include automatically delivering the therapy over a range of amplitudes (e.g., in a "sweep" process) while power is provided by an external signal generator. If the patient responds favorably, the patient can receive an implanted system, suitable for long-term treatment. This process is expected to take less time than stepping through many amplitudes during a trial period to determine which is best for the patient. Once the patient receives an implanted system, the manner in which the signal is delivered can be adjusted. In particular, the amplitude sweep technique will likely cause the patient to receive electrical stimulation at one or more amplitudes that are therapeutically effective, and one or more amplitudes that are not. While this is not an issue during the screening process (when the signal generator is typically external and power is readily available), during a chronic treatment program (when the signal generator is implanted) it is often desirable to conserve power to reduce the frequency with which the patient recharges the system batteries. Accordingly, the practitioner may focus the long term or chronic therapy on only the amplitude(s) that have been demonstrated (or are expected to demonstrate) effective therapeutic results. The duty cycle of the signal can then be reduced so as to reduce the power required by the implanted signal generator. This in turn can increase the length of time the implanted stimulator operates without recharging. In other embodiments, e.g., embodiments for which power consumption and/or the time between recharging events is not as important, the patient can receive therapy via amplitude sweeps over an extended period of time, independent of whether the sweep process was used to screen the patient.

In particular embodiments, the systems and methods disclosed herein are applicable to "high frequency," paresthesia-free SCS systems. Such SCS systems, for example, inhibit, reduce, and/or eliminate pain via waveforms with high frequency elements or components (e.g., portions having high fundamental frequencies), generally with reduced or eliminated side effects. Such side effects can include unwanted motor stimulation or blocking, unwanted pain or discomfort, unwanted paresthesia, and/or interference with sensory functions other than the targeted pain. In a representative embodiment, a patient receives high frequency therapeutic signals with at least a portion of the therapy signal at a frequency of from about 1.5 kHz to about 100 kHz, or from about 2.5 kHz to about 100 kHz, or from about 1.5 kHz to about 50 kHz, or from about 1.5 kHz to about 10 kHz, or from about 1.5 kHz to about 20 kHz, or from about 3 kHz to about 20 kHz, or from about 3 kHz to about 50 kHz, or from about 5 kHz to about 15 kHz, or at frequencies of about 8 kHz, 9 kHz, or 10 kHz. These frequencies are significantly higher than the frequencies associated with standard conventional "low frequency" SCS, which are generally below 1,200 Hz, and more commonly below 100 Hz. Accordingly, stimulation at these and other representative frequencies (e.g., from about 1.5 kHz to about 100 kHz) is occasionally referred to herein as high frequency modulation or stimulation. As will be discussed later, other embodiments are directed to generally paresthesia-free SCS systems and therapies, regardless of frequency.

The disclosed embodiments can provide simplified procedures for initially determining if a patient is a responder. As used herein, the term "responder" refers generally to a patient who responds favorably to a particular therapeutic technique and/or system. Specific details of certain embodiments of the technology are described below with reference to methods for stimulating one or more target neural populations (e.g., nerves) or sites of a patient, and associated implantable and external structures for providing the stimulation. Although selected embodiments are directed to stimulating the dorsal column, dorsal horn, dorsal root, dorsal root entry zone, and/or other particular regions of the spinal column to control pain, the stimulation may in some instances be directed to other neurological structures and/or target other neural populations of the spinal cord. Some embodiments can have configurations, components or procedures different than those described in this section, and other embodiments may eliminate particular components or procedures. Accordingly, the present technology may encompass other embodiments with additional elements and/or steps, and/or may encompass other embodiments without several of the features or steps shown and described below with reference to FIGS. 1A-6D.

In general terms, aspects of many of the following embodiments are directed to simplifying the determination of whether a patient is responsive to the therapeutic effects of paresthesia-free SCS therapies, thereby allowing permanent implantation of a signal generator in less time than is required for conventional procedures. As such, it is expected that the techniques described below with reference to FIGS. 1A-6D can provide paresthesia-free SCS therapy deployment procedures that are more efficient, in terms of time and/or cost, than existing deployment procedures associated with conventional, paresthesia-based SCS therapies. It is also expected that the described techniques can reduce the risk of infection associated with existing extended trial periods. Still further embodiments are directed to long-term, multi-amplitude therapies, whether or not such therapies are also used as a screening tool during a trial period.

As described above, a form of high frequency SCS therapy has been developed that does not cause paresthesia. Further, it has been found that there may be a delay before high frequency SCS provides a patient with effective pain relief. Therefore, the patient and practitioner may not immediately know if a patient is a responder to the high frequency SCS therapy. This situation does not exist with conventional SCS because the paresthesia generated by conventional SCS results in an immediate or near-immediate response in the patients, although the optimal settings may take some time to determine. Accordingly, conventional SCS deployment techniques include testing various signal amplitudes in sequence to determine which produces pain relief. Such techniques are not efficient for high frequency SCS screening. In particular, high frequency SCS deployment techniques include waiting a delay period (usually 1-2 days) at each amplitude setting and repeating the process at a new amplitude setting until pain relief is achieved. Consequently, conventional trial period processes can take weeks (depending on the number of amplitudes tested) when used in the context of some high frequency therapy techniques. Embodiments of the technology disclosed herein can provide an advantage over conventional techniques by sweeping through multiple signal amplitudes at a rate that allows a therapeutically effective treatment to be detected, without the patient perceiving or detecting therapy gaps produced when the signal is delivered at a therapeutically ineffective amplitude.

2.0 Representative Systems

FIG. 1A schematically illustrates a patient 190 and representative patient therapy system 100 for providing relief from chronic pain and/or other conditions, arranged relative to the general anatomy of the patient's spinal column 191. The system 100 can include a signal generator 101 (e.g., a pulse generator), which may be implanted subcutaneously within the patient 190 and coupled to one or more signal delivery elements or devices 110. The signal delivery elements or devices 110 may be implanted within the patient 190, typically at or near the patient's spinal cord midline 189. The signal delivery devices 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or a lead body or bodies 111 (identified individually as a first lead 111*a* and a second lead 111*b*). As used herein, the terms lead and lead body include any of a number of suitable substrates and/or support members that carry devices for providing therapy signals to the patient 190. For example, the lead or leads 111 can include one or more electrodes or electrical contacts (described further below with reference to FIG. 1B) that direct electrical signals into the patient's tissue, for example, to provide for patient pain relief. In other embodiments, the signal delivery devices 110 can include structures other than a lead body (e.g., a paddle) that also direct electrical signals and/or other types of signals to the patient 190.

The signal generator 101 can transmit signals (e.g., electrical signals) to the signal delivery devices 110 that up-regulate (e.g., excite) and/or down-regulate (e.g., suppress) target nerves. As used herein, and unless otherwise noted, the terms "modulate," "modulation," "stimulate," and "stimulation" refer generally to signals that have either of the foregoing types of effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing stimulation signals, providing guidance information for positioning the signal delivery devices 110, and/or executing other associated functions can be performed automatically by computer-executable instructions contained by computer-readable media located at the pulse generator 101 and/or other system components. Such processes can be performed as part of an overall screening process (e.g., to distinguish responders from non-responders) and/or as part of a longer term therapy regimen (e.g., for patients who have been identified as responders or potential responders). The signal generator 101 can include multiple portions, elements, and/or subsystems (e.g., for directing signals in accordance with multiple signal delivery parameters), carried in a single housing, as shown in FIG. 1A, or in multiple housings. In any of these embodiments, the signal generator 101 (and/or an external trial modulator 105, described further below) can automatically execute one or more programs. For example, during a trial period, the external trial stimulator 105 can automatically apply a signal over a range of amplitudes to one, two, several, all, or a significant subset (e.g., 50% or 75%) of the electrical contacts available for treating the patient.

The signal generator 101 can also receive and respond to an input signal received from one or more sources. The input signals can direct or influence the manner in which the therapy instructions are selected, executed, updated and/or otherwise performed. Accordingly, the input/output devices 112 can include one or more sensors (one is shown schematically in FIG. 1 for purposes of illustration) that are carried by the signal generator 101 and/or distributed outside the signal generator 101 (e.g., at other patient locations) while still directing input signals to, and/or otherwise communicating with, the signal generator 101. The sensors can provide inputs that depend on or reflect patient state (e.g., patient position, patient posture and/or patient activity level), and/or inputs that are patient-independent (e.g., time). Still further details are included in co-pending U.S. Pat. No. 8,355,797, incorporated herein by reference in its entirety.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use. In one embodiment, the external power source 103 can by-pass an implanted signal generator (e.g., eliminating the need for the implanted signal generator) and generate a therapy signal directly at the signal delivery device 110 (or via signal relay components). Such a signal generator can be configured for long-term use, e.g., by having a wearable configuration in which it is continuously available to direct the therapy signal to the implanted signal delivery device.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery devices 110 during an initial portion of the procedure, prior to implanting the signal generator 101. For example, a practitioner (e.g., a physician and/or a company representative) can use the trial modulator 105 to vary the stimulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In a typical process, the practitioner uses a cable assembly 120 to temporarily connect the trial modulator 105 to the signal delivery devices 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed, or may be performed automatically, as discussed in greater detail later.

The pulse generator 101, the lead extension 102, the trial modulator 105 and/or the connector 122 can each include a receiving element 109. Accordingly, the receiving elements 109 can be implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105, and/or the connector 122. The receiving elements 109 can be at least generally similar in structure and function to those described in U.S. Patent Publication No. 2013/0116754, which is incorporated herein by reference in its entirety.

After the signal delivery elements 110 are implanted, the patient 190 can receive therapy via signals generated by the trial modulator 105, generally for a limited period of time. Traditionally, the patient 190 receives such therapy for one week. However, with the deployment methods disclosed herein, this time may be reduced, e.g., to about 1-2 days. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with signal delivery parameters, e.g., selected based on the experience gained during the trial period and/or other sources. Optionally, the practitioner can also replace the signal delivery elements 110. Once the implantable signal generator 101 has been positioned within the patient 190, the signal delivery parameters provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude.

In any of the foregoing embodiments, the parameters in accordance with which the signal generator 101 provides signals can be adjusted during portions of the therapy regimen. For example, the frequency, amplitude, pulse width and/or signal delivery location can be adjusted in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. Certain aspects of the foregoing systems and methods may be simplified or eliminated in particular embodiments of the present disclosure. Further aspects of these and other expected beneficial results are detailed in co-pending U.S. Application Publication No. US2010/0274317; U.S. Pat. No. 8,712,533; and U.S. Patent Application Publication No. US2009/0204173, all of which are incorporated herein by reference in their entireties.

Figure 1B:
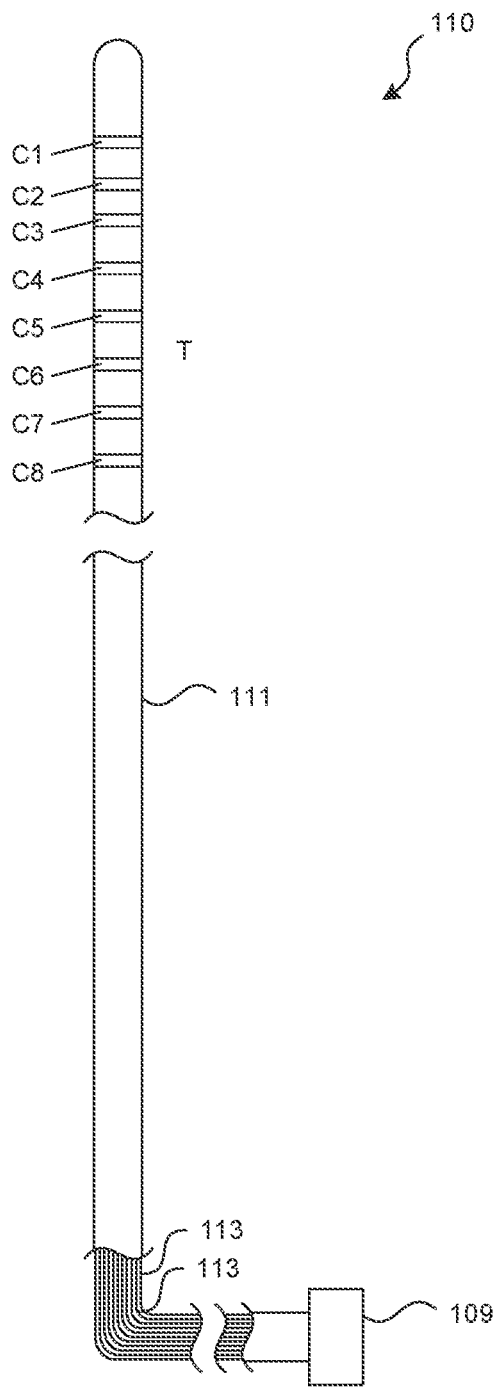
FIG. 1B is a partially schematic illustration of a representative signal delivery device configured in accordance with an embodiment of the present technology.

FIG. 1B is a partially schematic illustration of a representative signal delivery device 110, including a lead 111 configured in accordance with an embodiment of the present technology. The lead 111 carries multiple (e.g., eight) signal delivery contacts, identified as contacts C1-C8. The contacts C1-C8 are electrically connected to a receiving element 109 via corresponding conductors 113 (e.g., single- or multi-filer wires). Accordingly, each of the contacts C1-C8 can be individually addressable, and can be activated or not activated depending upon the signals received from the pulse generator 101 or 105 (FIG. 1A).

3.0 Representative Amplitude Adjustments

A form of high frequency SCS therapy has recently been determined to deliver therapy without generating paresthesia or unwanted pain or other sensory or motor effects to achieve effective therapy. (Such high frequency SCS therapy is described in more detail in the above-incorporated U.S. Pat. No. 8,712,533.) Aspects of the present technology are directed to techniques and systems for detecting whether a patient is a responder, despite the absence of paresthesia. For example, in accordance with embodiments of the present technology, the practitioner can activate a pulse generator to automatically scan or step through multiple amplitudes for the therapy signal. As a result, the patient will receive therapy over a wide range of amplitudes in a short period of time. Some of the amplitudes are likely to be ineffective, but as long as at least one amplitude is effective, the process serves the purpose of quickly distinguishing responders from non-responders. This is unlike conventional SCS techniques, which typically require an iterative amplitude-by-amplitude trial and error process to determine whether or not the patient is a responder to any of a multitude of amplitudes. If this process were to be attempted using conventional SCS, the patient would typically be subjected to sensations of paresthesia that come and go, which would annoy, distract and/or frustrate the patient without providing a clear indication as to whether or not the patient is a responder.

Figure 2:
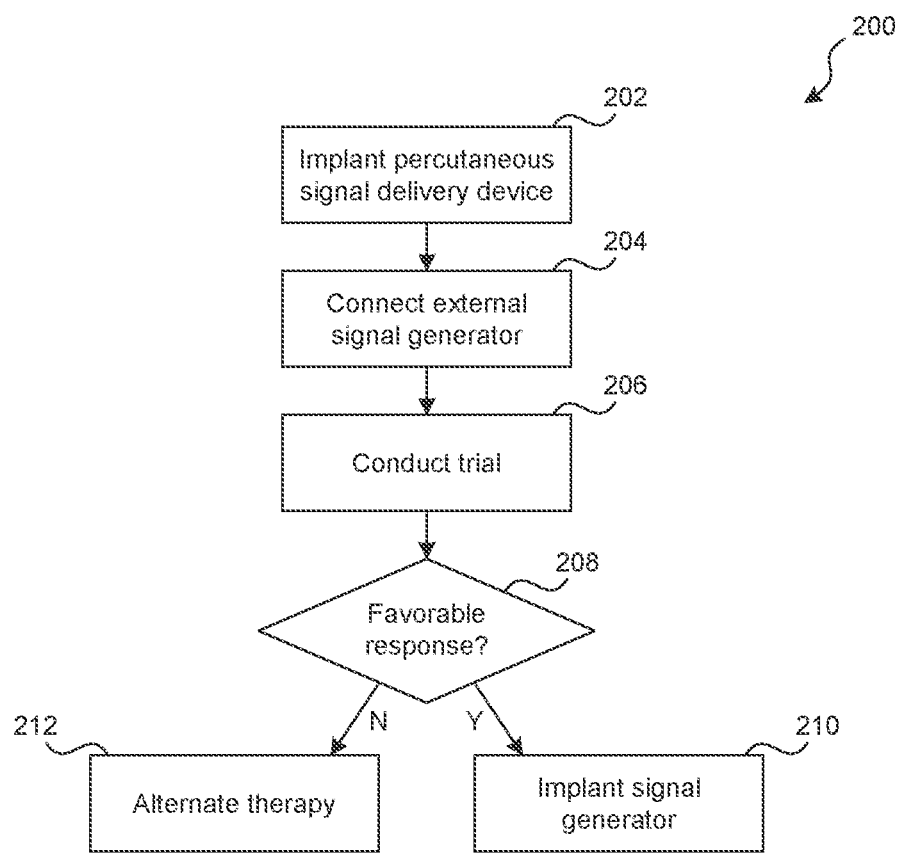
FIG. 2 is a flow diagram illustrating a representative method for identifying responders in accordance with an embodiment of the present technology.

FIG. 2 is a flow diagram of a process 200 suitable for deploying a non-paresthesia-generating patient therapy system, in accordance with an embodiment of the present technology. Block 202 includes implanting a percutaneous signal delivery device, for example, an elongated lead, paddle, or other device configured to deliver therapeutic electrical signals to a patient. In some embodiments, a single signal delivery device is implanted in the patient, and in other embodiments, two or more signal delivery devices are implanted in the patient. For example, the patient can receive two signal delivery devices, one on each side of the spinal cord midline, as shown in FIG. 1A. Block 204 includes connecting the signal delivery device(s) to an external signal generator, for example, the external signal generator 105 described above with reference to FIG. 1A. The foregoing steps provide a set-up suitable for conducting a trial to determine whether a given patient responds to the electrical therapy or not.

In block 206, a practitioner conducts the trial. As will be described in greater detail later, at least a portion of the trial can include varying the amplitude at which an electrical therapy signal is delivered to the patient, and in particular, delivering the signal at all likely amplitudes so as to determine whether the patient is a responder or likely responder to the therapy. This determination is made in block 208. If the patient is a responder, block 210 includes implanting a signal generator to provide long-term therapy to the patient. If the patient does not respond, then block 212 can include identifying an alternate therapy.

Figure 3:
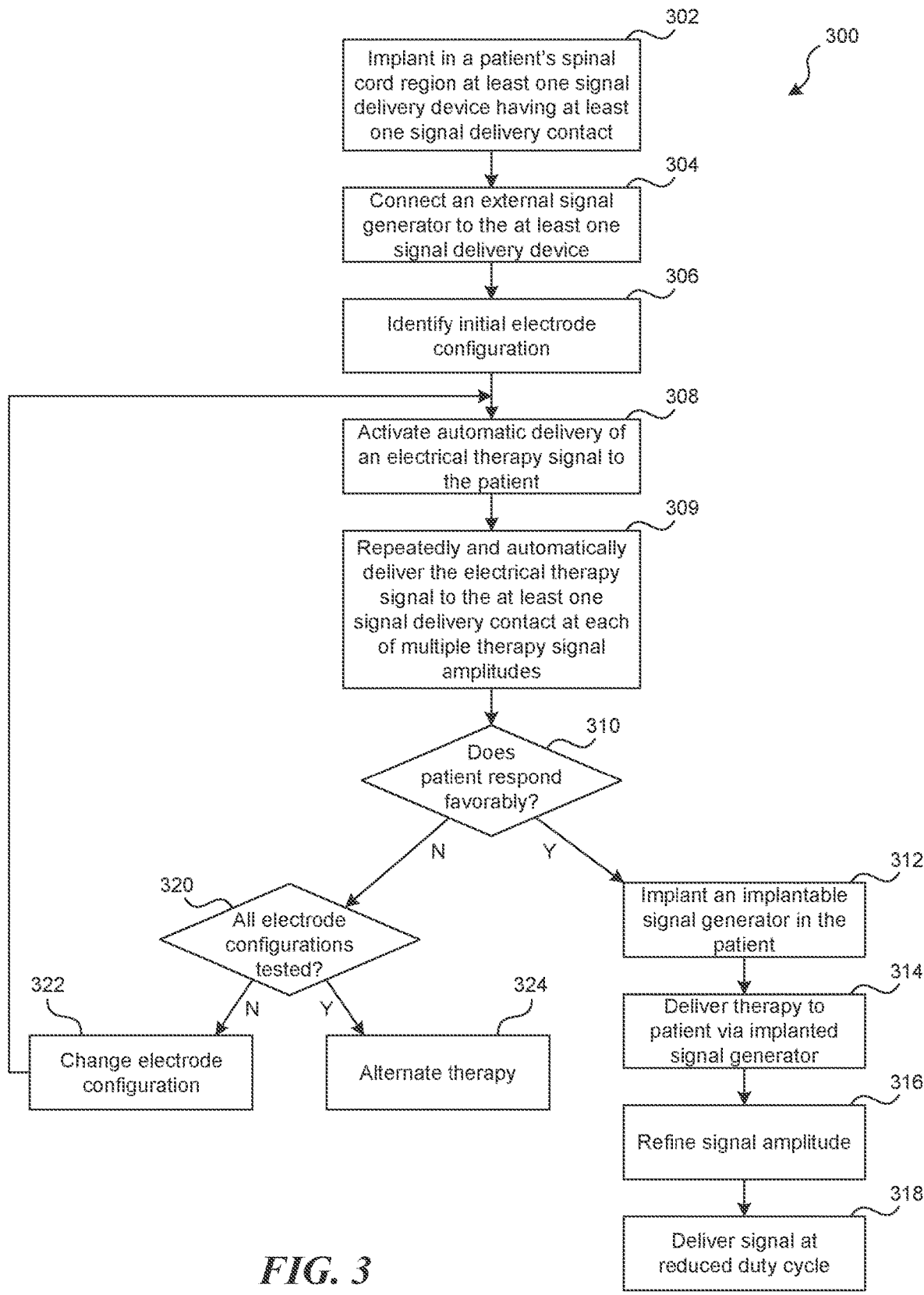
FIG. 3 is a flow diagram illustrating a representative method for identifying responders in accordance with another embodiment of the present technology.

FIG. 3 is a flow diagram illustrating a process 300 conducted in accordance with another embodiment of the present technology. Block 302 includes implanting at least one signal delivery device, having at least one signal delivery contact, in a patient's spinal cord region. For example, block 302 can include implanting a signal delivery lead in an epidural location proximate to the patient's spinal cord, e.g., close enough to deliver an effective therapy signal. Typically, the at least one signal delivery contact will be within several millimeters or centimeters of the target neural population. The lead can be located along the spinal cord midline or off the spinal cord midline, within the epidural space. In other embodiments, the lead or other signal delivery device can be implanted outside the vertebrae defining the spinal canal, and in still further embodiments, the signal delivery device can be implanted (e.g., percutaneously) in other locations. In any of these embodiments, the signal delivery device is in close enough proximity to one or more target neural populations to produce a therapeutic effect.

Block 304 includes connecting an external signal generator to the at least one signal delivery device. Block 306 includes identifying an initial electrode configuration. For example, referring to FIG. 1B, a practitioner can select contacts C5 and C6 to operate as an anode and cathode (e.g., a bipole) for delivering an electrical therapy signal to a target neural population. This selection process can be conducted based on the practitioner's understanding of where the most likely target neural population lies, relative to the contacts of the implanted signal delivery device. In other embodiments, the contact selection process can be automated, e.g., via a system that automatically identifies the relative locations of the signal delivery device and the target neural population.

In still further embodiments, all the electrodes or a substantial or significant subset (e.g., at least half) of the electrodes can be activated simultaneously. This arrangement can eliminate, as a variable, whether a particular electrode is active or inactive.

Once the initial electrode configuration has been identified, the process includes activating automatic delivery of an electrical therapy signal to the patient (block 308), via the one more contacts identified at block 306. This process can include turning on the signal generator, reactivating the signal generator (e.g., if it was in an inactive state), and/or otherwise causing electrical therapy signals to be delivered to the patient. The delivery process can include repeatedly and automatically delivering the electrical therapy signal to the selected signal delivery contact(s) at each of multiple therapy signal amplitudes (block 309). In particular, block 309 can include rapidly stepping or sweeping through multiple amplitudes, any one or more of which are expected to produce a favorable patient response. This approach can make use of at least two observed effects associated with high frequency electrical therapy signals. First, properly selected high frequency signals do not produce paresthesia (or other sensory responses) in the patient. Accordingly, the patient will receive no sensory feedback (other than pain reduction) even though the signal amplitudes are changing. Second, high frequency therapy has been observed to be effective even at duty cycles significantly below 100%. In particular, patients have reported favorable pain reduction outcomes at duty cycles of less than 20% or less than 15% or less than 10%. Accordingly, the fact that the therapy signal may have a therapeutically effective amplitude for only a fraction of the time that it is delivered, is not expected to impact whether or not the patient reports a successful outcome.

Block 310 includes determining whether the patient has responded favorably to the amplitude sweep conducted in block 309. Block 310 can accordingly include receiving feedback from the patient indicating whether or not, (and to what extent) the patient's pain has been reduced. Because high frequency therapy has been observed to have a delayed effect, the patient may receive therapy for a period of time of several hours, one day, or more than one day (e.g., two days) before it can be conclusively determined whether or not the patient is a responder.

If the patient fails to respond, block 320 includes determining whether all electrode configurations have been tested. If not, the electrode configuration is changed (block 322) and the process of automatically delivering the electrical therapy signal to the patient (block 308) is resumed. If all possible electrode configurations have been tested (e.g., in a sequential manner or by testing all electrodes simultaneously), then block 324 can include seeking an alternate therapy.

If, in block 310, the patient does respond favorably, block 312 includes implanting an implantable signal generator in the patient, as part of a long-term treatment regimen, e.g., for treating chronic pain. Block 314 includes delivering therapy to the patient via the implanted signal generator. In one aspect of this embodiment, the patient can continue to receive a varying amplitude signal, e.g., one that includes therapeutically beneficial amplitudes and amplitudes that may not be therapeutically beneficial. This approach can be used because, even if not therapeutic, such amplitudes are not expected to be physiologically detrimental. Alternatively, it may be desirable to refine the amplitudes (and/or other signal delivery parameters) in accordance with which the therapy is delivered, so as to focus on only effective parameters. This process is indicated at block 316. During this process, the patient can receive therapies at each of multiple amplitudes, for a period of time long enough (e.g., at least several hours, or at least one day) to determine more precisely which amplitudes are effective and which are not. The amplitudes tested during this process (e.g., a second set of amplitudes) may be the same as or different than the amplitudes tested during the trial or screening process described above (e.g., a first set of amplitudes). Accordingly, this process may take several days or weeks. A benefit of the process is that the signal can then be delivered at a reduced duty cycle (block 318) because time spent delivering the signal at ineffective amplitudes is reduced or eliminated. Accordingly, the amount of power required to deliver effective therapy to the patient can be reduced, which in turn can reduce the frequency with which the patient recharges the implantable signal generator.

As indicated above, signal delivery parameters other than amplitude can be adjusted at block 316. For example, if all (or a significant subset) of the signal delivery contacts at the signal delivery device were activated during the trial process, the number of active electrodes can be reduced as part of the process at block 316.

Figure 4:
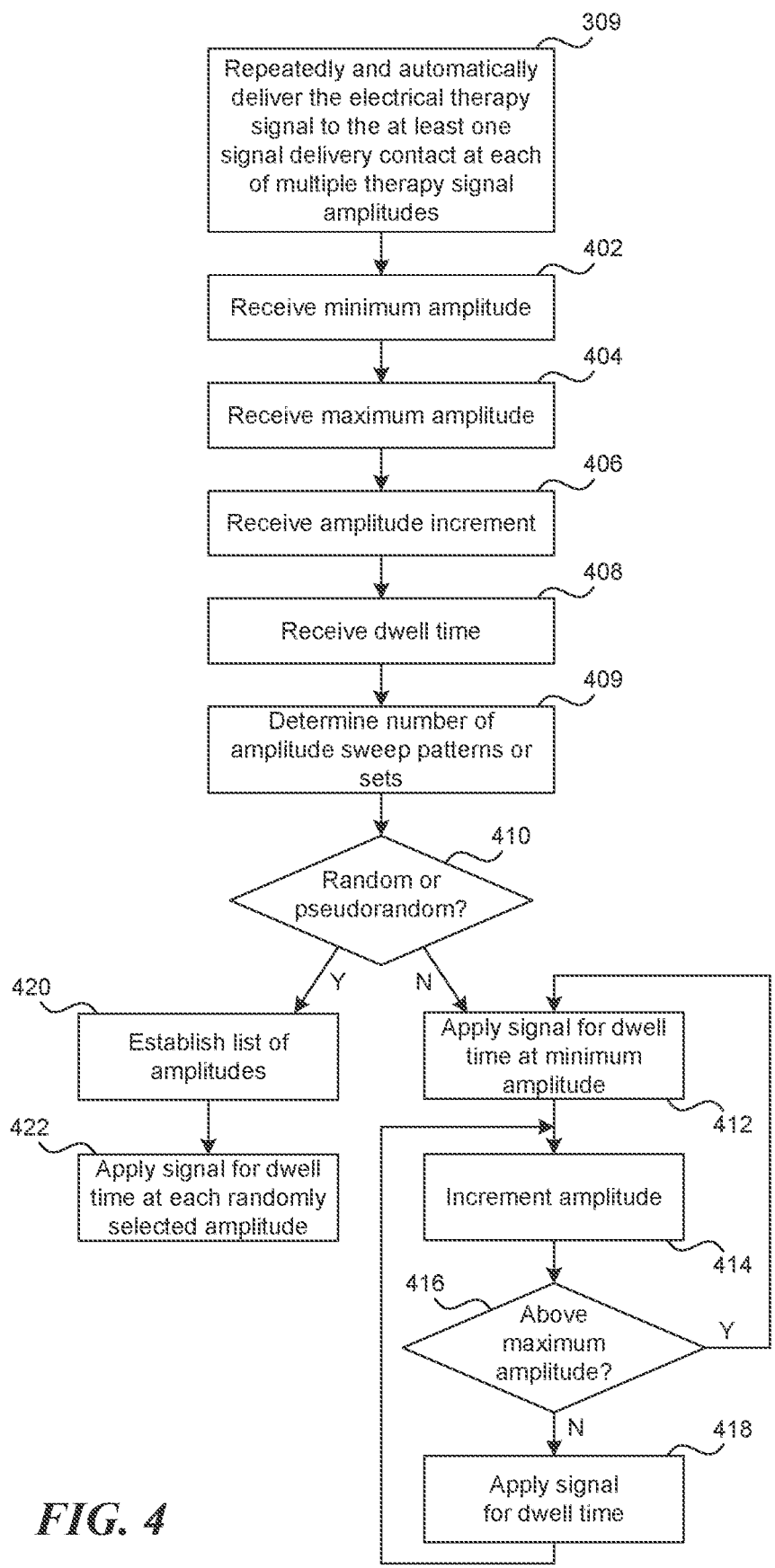
FIG. 4 is a flow diagram illustrating a method for varying the amplitude of a signal applied to a patient in accordance with an embodiment of the present technology.

FIG. 4 is a block diagram illustrating details of several embodiments for repeatedly and automatically delivering the electrical therapy signal, as described in the context of block 309 in FIG. 3. Block 402 includes receiving a first or minimum amplitude, and block 404 includes receiving a second or maximum amplitude. The minimum amplitude can be selected based on prior experience and/or other factors. In a representative embodiment, the minimum amplitude for a high frequency signal can be selected to be about 0.1 mA, 0.2 mA, 0.3 mA, 0.4 mA, 0.5 mA, or about 1 mA. The maximum amplitude can also be selected based on prior clinical experience, or other factors. In representative embodiments, the maximum amplitude can be selected at 10 mA (even though the amplitude range of the device delivering the therapy may be greater). In further embodiments, the maximum amplitude can be selected at a lower value, for example, 3.5 mA or 5 mA. In yet further embodiments, the maximum amplitude can be selected on a patient-by-patient basis, e.g., by determining the sensory threshold amplitude for an individual patient. In any of the foregoing embodiments, the variables can be pre-established, e.g., by a practitioner on a case-by-case basis, or via a pre-programmed memory register.

Block 406 includes receiving an amplitude increment, and block 408 includes receiving a dwell time. The amplitude increment corresponds to the difference between successively increasing amplitudes. Representative values include 0.1 mA, 0.2 mA, 0.3 mA, 0.4 mA and 0.5 mA. The dwell time refers to the amount of time spent at any one amplitude. Representative dwell times include a single bi-phasic pulse pair, a number of multiple, consecutive pulse pairs, or a set time period (e.g., one second, 10 seconds, 20 seconds, 30 seconds, 60 seconds, one hour, several hours, one day, or several days). The foregoing values are then used to determine the number of amplitude sweep patterns or sets necessary to determine whether the patient is a responder or not (block 409). For example, it may be desirable to deliver the therapy at no less than a 20% duty cycle for each amplitude. If the difference between the minimum amplitude and maximum amplitude, combined with the amplitude increment, produces five amplitude values or less, a single sweep pattern will deliver each amplitude for 20% or more of the time. If the foregoing factors produce more than five amplitude values, block 409 can include breaking up the amplitude sweep into multiple sweep patterns or sets, each of which is delivered serially as part of the overall trial or screening process. The patient then undergoes a first responder test period (trial period) to determine if he/she responds to the first amplitudes, and a second responder test period (trial period) to determine if he/she responds to the second amplitudes.

In other embodiments, the relevant time interval for signal delivery at each amplitude can be specified in other manners. For example, the process can include receiving an amplitude sweep period (from a user, or a pre-programmed memory register). The amplitude sweep period corresponds to the smallest period of time over which a repeating pattern of amplitudes occurs. The process can then include determining the number of pulses at each amplitude that fit within the amplitude sweep period. If the number of pulses produces a duty cycle that is too short for each amplitude to be tested, the program can break the amplitudes up to occur over multiple amplitude sweep periods. As discussed above, the patient then undergoes a first responder test period (trial period) to determine if he/she responds to the first amplitudes, and a second responder test period (trial period) to determine if he/she responds to the second amplitudes.

The result of the foregoing process is a number of amplitudes to be tested on the patient. Representative numbers include three, five, 10 or 20 amplitudes.

Block 410 includes determining whether the amplitude sweeps are to be conducted in an organized, stepped fashion, or in a random or pseudorandom fashion. If the amplitude sweep is to be conducted in a random or pseudorandom fashion, block 420 includes establishing a list of amplitudes (based on the minimum amplitude, maximum amplitude, and amplitude increment), and block 422 includes applying the therapy signal for the selected dwell time at each randomly selected amplitude.

If the amplitude sweep is to be conducted in a stepped fashion, block 412 includes initially applying the therapy signal for the dwell time at the minimum amplitude. In block 414, the amplitude is incremented. In block 416, the process determines whether the incremented amplitude is above the maximum amplitude. If it is not, then the signal is applied at the incremented amplitude for the dwell time (block 418), and the amplitude is incremented again. If the incremented amplitude is above the maximum amplitude, then the process returns to block 412. Accordingly, blocks 412-418 describe a process for sweeping through the amplitude range by delivering each amplitude at the requested dwell time, and then repeating.

Figure 5:
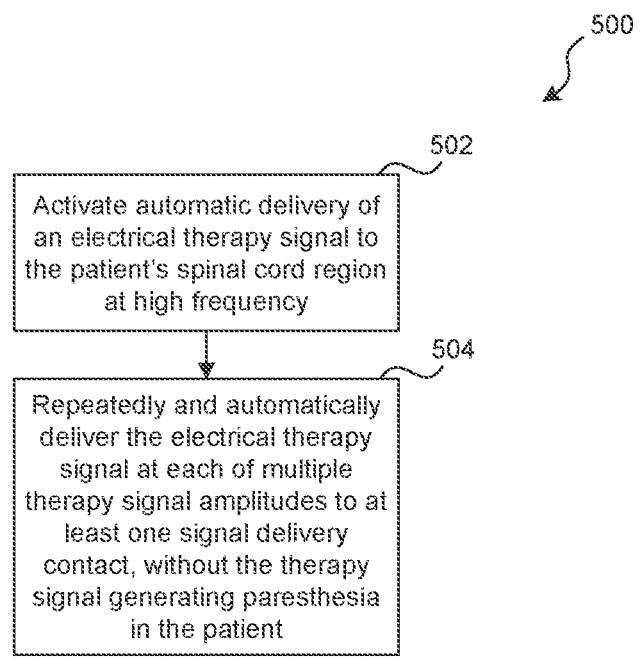
FIG. 5 is a flow diagram illustrating a process for automatically delivering therapy in accordance with an embodiment of the present technology.

The foregoing techniques described above with reference to FIGS. 2-4 include using the amplitude sweep process for determining whether a patient is a responder or not. In other embodiments, the amplitude sweep process can be used as part of a long-term therapy regimen, independent of whether it is also used to screen responders from nonresponders. For example, FIG. 5 illustrates a process 500 for delivering therapy in such a manner. Block 502 includes activating automatic delivery of an electrical therapy signal to the patient's spinal cord region at a high frequency (e.g., in a frequency range between 1.5 kHz and 100 kHz). Block 504 includes repeatedly and automatically delivering the electrical therapy signal at each of multiple therapy signal amplitudes, without the therapy signal generating paresthesia in the patient. Accordingly, for situations in which it may not be desirable to isolate a particularly effective amplitude (e.g., if a reduced duty cycle and therefore required power level are of less significance), the process can include sweeping through multiple amplitudes, both effective and non-effective, during the course of long-term treatment.

Figure 6A:
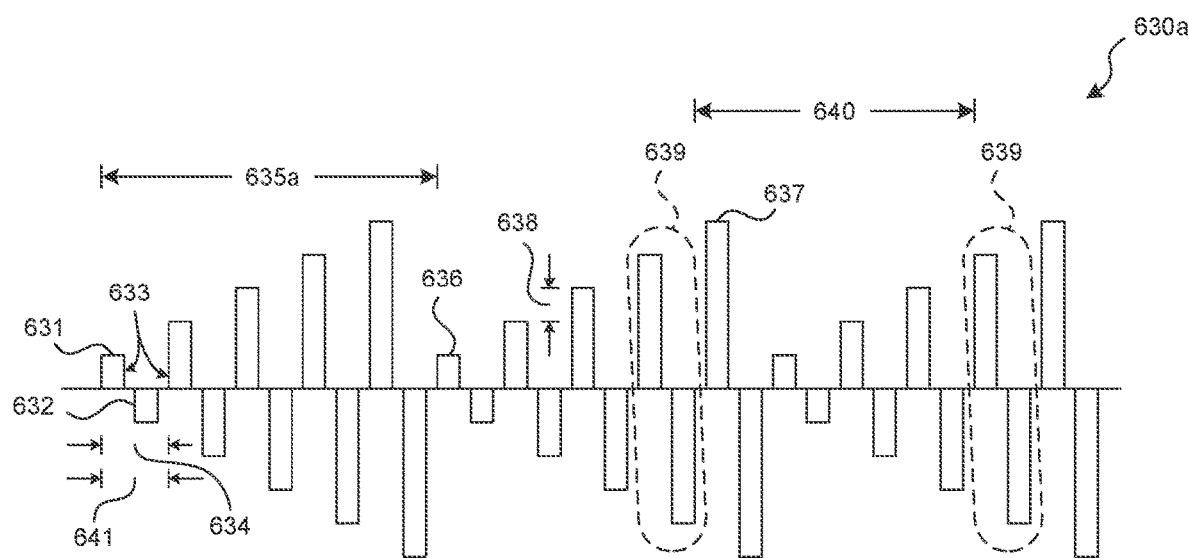
FIGS. 6A-6D illustrate representative waveforms for delivering therapy to patients in accordance with embodiments of the present technology.

FIGS. 6A-6D are partially schematic, graphical illustrations of waveforms having characteristics in accordance with representative embodiments of the present technology. FIG. 6A illustrates a first waveform 630a that includes multiple anodic pulses 631 and cathodic pulses 632 delivered in the form of multiple, sequential, bi-phasic pulse pairs. Individual anodic and cathodic pulses may be separated by an interpulse interval 633. Two bipolar pulses, e.g., a single anodic pulse 631 and a single cathodic pulse 632, together with an intervening and following interpulse interval 633 (if present), define a pulse period 634. The frequency of the signal is then the inverse of the pulse period 634.

As shown in FIG. 6A, the amplitudes of the pulses are monotonically incremented by an amplitude increment 638 from a minimum amplitude 636 to a maximum amplitude 637. The sweep is then repeated by returning to the minimum amplitude 636, e.g., in a single step. The amount of time required to deliver a single sweep (e.g., the shortest combination of amplitudes that are repeated over and over) corresponds to a first amplitude sweep period 635a. The dwell time 641 (e.g., the amount of time spent at a given amplitude during a given amplitude sweep period 635a) corresponds to the pulse period 634, in the embodiment shown in FIG. 6A.

FIG. 6A also illustrates therapeutically effective pulses 639, e.g., pulses that produce an effective therapy in the patient. In the illustrated example, such pulses are limited to a single amplitude, and are separated by an effective pulse gap 640. The maximum effective pulse gap 640 (assuming at least one amplitude is effective) represents the amount of time the patient is not receiving the therapy signal at an effective amplitude. In the illustrated example, the effective pulse gap 641 is approximately the same as the first amplitude sweep period 635a. If more than one amplitude is effective, the effective pulse gap will be shorter.

Figure 6B:
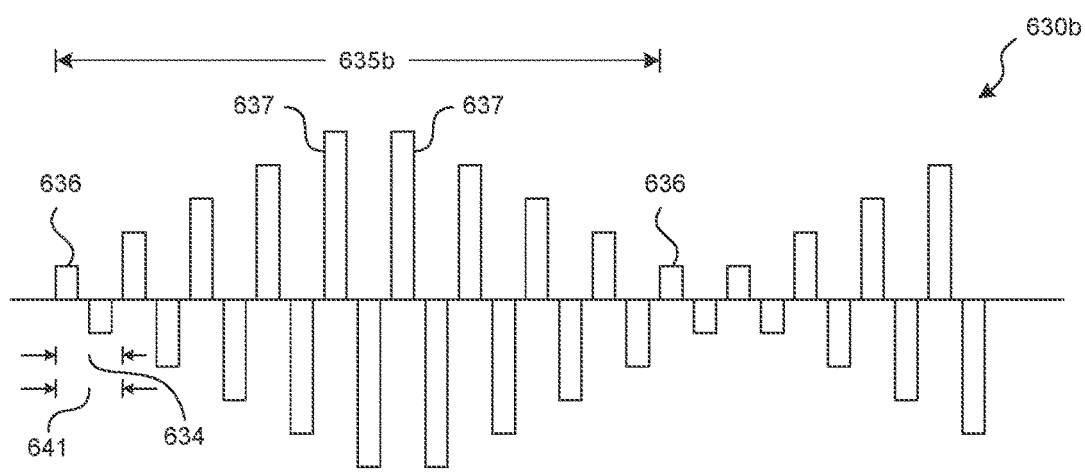

In the representative embodiment shown in FIG. 6A, the first amplitude sweep period 635a includes a monotonically increasing amplitude up to the maximum amplitude 637, followed by a single step reduction to the minimum amplitude 636. In other embodiments, the amplitudes can be increased and/or decreased in other manners. For example, FIG. 6B illustrates a second waveform 630b in which the amplitude is increased monotonically from the minimum amplitude 636 to the maximum amplitude 637, and is then decreased monotonically back to the minimum amplitude 636. In this case, a second amplitude sweep period 635b is twice the first amplitude sweep period 635a described above with reference to FIG. 6A.

Figure 6C:
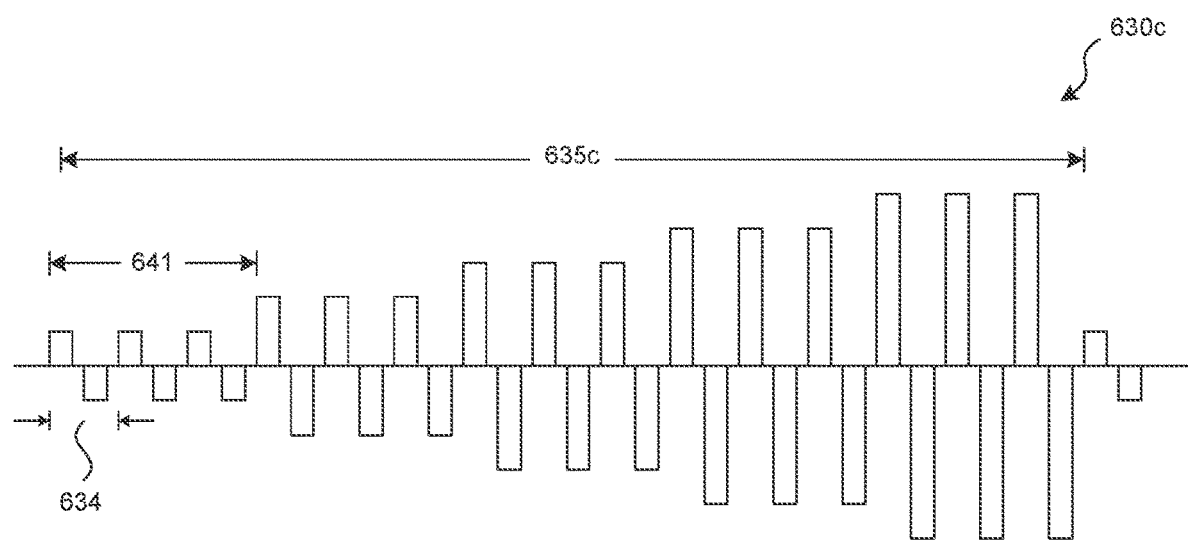

In each of the waveforms 630a, 630b described above, the dwell time 641 corresponds to a single pulse period 634. FIG. 6C illustrates a third representative waveform 630c in which the dwell time 641 corresponds to three pulse periods 634. As a result, a third amplitude sweep period 635c is three times the first amplitude sweep period 635a shown in FIG. 6A.

Figure 6D:
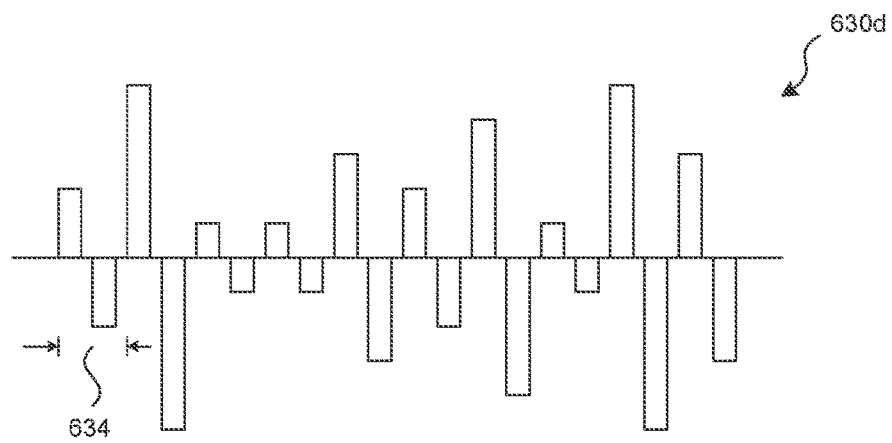

FIG. 6D illustrates still another representative waveform 630d in which the biphasic pairs of pulses have amplitudes that vary in a random or pseudorandom manner. Because the amplitudes are varied in a random or pseudorandom manner, there is no readily definable amplitude sweep period; however, on average, each amplitude will be delivered for the same fraction of time as in the embodiments described above with reference to FIG. 6A-6C because the minimum amplitude 636, maximum amplitude 637 and amplitude increment 638 are the same across all four embodiments.

In any of the embodiments described above, the dwell time 641 can be selected to be at or above the minimum dwell time required to produce an effective therapy at any given amplitude. In addition, as discussed above, the fraction of time during which the signal is delivered at any particular amplitude is selected to be at or above the minimum duty cycle expected for that amplitude.

Further Representative Embodiments

Further representative embodiments of the presently disclosed technology are described below. One such embodiment includes a method for deploying a patient therapy system, that further includes implanting, in a patient's spinal cord region, at least one signal delivery device having at least one signal delivery contact. The method can further include connecting an external signal generator to the at least one signal delivery device, and activating automatic delivery of an electrical therapy signal to the patient. This can in turn include a process of repeatedly and automatically delivering the electrical therapy signal to the at least one signal delivery contact at each of multiple therapy signal amplitudes. If the patient responds favorably to receiving the automatically delivered electrical therapy signal (e.g., if the patient receives a therapeutic benefit), the process can further include implanting an implantable signal generator in the patient.

In particular embodiments, automatically delivering the electrical therapy signal includes automatically stepping from one therapy signal amplitude to another based on a pre-established amplitude increment. The signal can be delivered at a high frequency (e.g., a frequency in a range between 1.5 kHz and 100 kHz, 1.5 kHz and 50 kHz, 3 kHz and 15 kHz, or 10 kHz) and does not generate paresthesia in the patient, or in particular embodiments, any sensory effect on the patient. Once the signal generator is implanted, the process can include ceasing to automatically deliver the initial electrical therapy signal and can include activating delivery of a second electrical therapy signal at multiple amplitudes of a second set of therapy signal amplitudes. In this case, each amplitude may be delivered for a period of at least one day. Based on the results obtained from delivering the second electrical therapy signal, the process can include selecting an amplitude for additional therapy and activating the delivery of the electrical therapy at the selected signal amplitude.

The electrical therapy signal can include any of a number of suitable amplitudes and pulse widths, in suitable combination with any of the frequencies described herein. In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 microseconds to about 333 microseconds, about 10 microseconds to about 166 microseconds, about 20 microseconds to about 100 microseconds, about 30 microseconds to about 100 microseconds, about 30 microseconds to about 35 microseconds, and about 30 microseconds to about 40 microseconds. Further representative pulse widths include pulse widths from 10-50 microseconds, 20-40 microseconds, 25-35 microseconds, and 30 microseconds.

In a particular embodiment, the electrical therapy signal delivered to the patient is delivered at a frequency in a frequency range between 1.5 kHz and 100 kHz. The process of activating automatic delivery of the electrical therapy signal can include repeatedly and automatically stepping through multiple therapy signal amplitudes in an amplitude range between 0.5 mA and 3.5 mA, with the electrical therapy signal delivered only once at each amplitude during a period of two minutes. For example, as shown in FIG. 6C, the amplitude sweep period 635c can be two minutes long. The electrical therapy signal is delivered without generating paresthesia in the patient.

Representative patient therapy systems in accordance with the present technology can include a signal generator coupleable to at least one implantable signal delivery device having at least one signal delivery contact. A signal generator can be programmed with instructions that, when executed, direct a non-paresthesia-generating electrical therapy signal to the patient via the at least one signal delivery contact. The frequency of the electrical therapy signal can be in a frequency range between 1.5 kHz and 100 kHz. The signal can be repeatedly and automatically delivered at each of multiple therapy signal amplitudes to the same signal delivery contact.

One advantage of at least some of the foregoing features is that the amplitude sweep process can more quickly determine whether a patient is or is not a responder to a high frequency spinal cord stimulation program, despite the fact that the therapy typically does not produce paresthesia or other sensory effects. Accordingly, the process of determining whether a particular patient is a responder can be both cheaper and more efficient than other processes.

Another advantage of at least some of the foregoing embodiments is that the amplitude sweep arrangement may reduce or eliminate the likelihood for the patient to habituate to any given frequency. Because habituation is more likely to be an issue (if at all) during long-term treatment, this feature may be particularly beneficial during the chronic, implanted phase of treatment, rather than the screening or trial phase.

From the foregoing, it will be appreciated that specific embodiments of the technology have described herein for purposes of illustration, but that various modifications may be made without deviating from the technology. For example, the amplitude sweeps described above can include amplitude variations other than those specifically illustrated and described herein. In particular embodiments, the foregoing techniques can be applied to therapies other than high frequency therapies, that also produce therapeutic results without paresthesia or other sensory or motor effects. Representative examples include burst therapies and low frequency therapies applied to the patient's dorsal root ganglia.

In still further embodiments, the foregoing techniques can be used in the context of a signal generator that is external during the long-term treatment regimen (e.g., in addition to a trial period. Such a signal generator can transmit pulses (or energy for pulses) directly to an implanted signal delivery device through the patient's skin.

Certain aspects of the technology described in the context of particular embodiments may be combined or eliminated in other embodiments. For example, the amplitude sweep process may be conducted as part of a screening process, or as part of a long term therapy delivery process, or both. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein.

To the extent any materials incorporated by reference herein conflict with the present disclosure, the present disclosure controls. As used herein, the term "between" in the context of a range includes the endpoints of the range.

I claim:

1. A patient therapy system, comprising:
   a signal generator coupleable to at least one implantable signal delivery device, the signal generator programmed with instructions that, when executed (a) direct a non-paresthesia generating electrical signal to the patient via the implantable signal delivery device for a plurality of sequential amplitude sweep periods, and (b) step the electrical signal through multiple signal amplitudes of a same polarity for individual amplitude sweep periods of the plurality of sequential amplitude sweeps periods, wherein—
   at least some of the sequential amplitude sweep periods include at least some of the same multiple signal amplitudes, and
   pulses of the same amplitude in sequential amplitude sweep periods have a same pulse width.

2. The system of claim 1 wherein the multiple signal amplitudes are generated in a random order for each amplitude sweep period.

3. The system of claim 1 wherein the multiple signal amplitudes are generated in a same order for each amplitude sweep period.

4. The system of claim 1 wherein the individual amplitude sweep periods include at least three different signal amplitudes.

5. The system of claim 1 wherein the individual amplitude sweep periods include at least five different signal amplitudes.

6. The system of claim 1 wherein the multiple signal amplitudes each have an amplitude of between 0.5 mA and 10 mA.

7. The system of claim 1 wherein the individual amplitude sweep periods include two or more pulses at each of the multiple signal amplitudes.

8. The system of claim 1 wherein the individual amplitude sweep periods include a single pulse at each of the multiple signal amplitudes.

9. The system of claim 1 wherein the sequential amplitude sweep periods include the same multiple signal amplitudes.

10. The system of claim 1 wherein stepping the signal through the multiple amplitudes includes (a) increasing the amplitude of the signal over the individual amplitude sweep period, (b) decreasing the amplitude of the signal over the individual amplitude sweep period, or both (a) and (b).

11. The patient therapy system of claim 1 wherein the non-paresthesia generating electrical signal is a first non-paresthesia generating electrical signal, and wherein the instructions include instructions that, when executed, cause the signal generator to direct a second non-paresthesia generating electrical signal to the patient via the implantable signal delivery device at individual amplitudes of the multiple signal amplitudes to identify at least one therapeutically effective amplitude, in response to an indication that the patient responds favorably to the first non-paresthesia generating electrical signal.

12. A method of treating a patient, comprising:
   programming a signal generator to direct a non-paresthesia generating electrical signal to the patient via an implantable signal delivery device for a plurality of sequential amplitude sweep periods, including stepping the signal through multiple signal amplitudes of a same polarity for individual amplitude sweep periods of the plurality of sequential amplitude sweeps periods, and wherein—
   at least some of the sequential amplitude sweep periods include at least some of the same multiple signal amplitudes, and
   pulses of the same amplitude in sequential amplitude sweep periods have a same pulse width.

13. The method of claim 12 wherein the multiple signal amplitudes are generated in a random order for each amplitude sweep period.

14. The method of claim 12 wherein the multiple signal amplitudes are generated in a same order for each amplitude sweep period.

15. The method of claim 12 wherein the multiple signal amplitudes include at least three different amplitudes each having a value of between about 0.5 mA and about 10 mA.

16. The method of claim 12 wherein a step change between the adjacent amplitudes of the multiple signal amplitudes is between about 0.1 mA and about 0.5 mA.

17. The method of claim 12 wherein stepping the signal through the multiple signal amplitudes includes (a) increasing the amplitude of the signal over the individual amplitude sweep period, (b) decreasing the amplitude of the signal over the individual amplitude sweep period, or both (a) and (b).

18. The method of claim 12 wherein the individual amplitude sweep periods include two or more pulses at each of the multiple signal amplitudes.

19. The method of claim 12 wherein the individual amplitude sweep periods include a single pulse at each of the multiple signal amplitudes.

20. The method of claim 12 wherein the sequential amplitude sweep periods include the same multiple signal amplitudes.

21. The method of claim 12 wherein the non-paresthesia generating electrical signal is a first non-paresthesia generating electrical signal, and wherein the method further comprises:
   in response to receiving an indication that the patient responds favorably to the first non-paresthesia generating electrical signal, programming the signal generator to direct a second non-paresthesia generating electrical signal to the patient via the implantable signal delivery device at individual amplitudes of the multiple signal amplitudes to identify at least one therapeutically effective amplitude.

22. A method of treating a patient, comprising:
   programming a signal generator to direct a non-paresthesia generating electrical signal to the patient via an implantable signal delivery device for a plurality of sequential amplitude sweep periods, wherein—
   individual amplitude sweep periods of the plurality of sequential amplitude sweep periods include multiple signal amplitudes of a same polarity generated in a random order,
   at least some of the sequential amplitude sweep periods include at least some of the same multiple signal amplitudes, and
   pulses of the same amplitude in sequential amplitude sweep periods have a same pulse width.

23. The method of claim 22 wherein the individual amplitude sweep periods include at least three different signal amplitudes each having an amplitude of between about 0.5 mA and about 10 mA.

24. The method of claim 22 wherein the individual amplitude sweep periods include two or more pulses at each of the multiple signal amplitudes.

25. The method of claim 22 wherein the non-paresthesia generating electrical signal is a first non-paresthesia generating electrical signal, and wherein the method further comprises:

in response to receiving an indication that the patient responds favorably to the first non-paresthesia generating electrical signal, programming the signal generator to direct a second non-paresthesia generating electrical signal to the patient via the implantable signal delivery device at individual amplitudes of the multiple signal amplitudes to identify at least one therapeutically effective amplitude.

\* \* \* \* \*

UNITED STATES PATENT AND TRADEMARK OFFICE
CERTIFICATE OF CORRECTION

PATENT NO. : 11,944,817 B2
APPLICATION NO. : 17/900681
DATED : April 2, 2024
INVENTOR(S) : Chris Dawson It is certified that error appears in the above-identified patent and that said Letters Patent is hereby corrected as shown below:

On the Title Page

On the page 4, in Column 2, Item (56) under "U.S. Patent Documents", Line 23, delete "Zhu" and insert -- Zhu et al. --.

On the page 4, in Column 2, Item (56) under "U.S. Patent Documents", Line 24, delete "Grandhe" and insert -- Grandhe et al. --.

In the Specification

In Column 1, Line 13, delete "a" and insert -- are --.

In Column 12, Line 65, delete "FIG." and insert -- FIGS. --.

Signed and Sealed this
Twentieth Day of August, 2024

Katherine Kelly Vidal
*Director of the United States Patent and Trademark Office*